US012714842B2

(12) United States Patent
Bond et al.

(10) Patent No.: US 12,714,842 B2
(45) Date of Patent: Aug. 25, 2026

(54) ACCESS SYSTEM FOR A MEDICAL TREATMENT DEVICE FOR EXTRACTING OR ADDING A MEDICAL LIQUID, AND MEDICAL TREATMENT DEVICE HAVING AN ACCESS OF THIS KIND

(71) Applicant: FRESENIUS MEDICAL CARE DEUTSCHLAND GMBH, Bad Homburg (DE)

(72) Inventors: Oliver Bond, Heidenfeld (DE); Matthias Brandl, Bad Konigshofen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 321 days.

(21) Appl. No.: 18/700,275

(22) PCT Filed: Oct. 7, 2022

(86) PCT No.: PCT/EP2022/077972
§ 371 (c)(1),
(2) Date: Apr. 11, 2024

(87) PCT Pub. No.: WO2023/061881
PCT Pub. Date: Apr. 20, 2023

(65) Prior Publication Data

US 2025/0177717 A1 Jun. 5, 2025

(30) Foreign Application Priority Data

Oct. 14, 2021 (DE) ..................... 10 2021 126 702.1

(51) Int. Cl.

| | |
|---|---|
| ***A61M 39/18*** | (2006.01) |
| ***A61L 2/10*** | (2026.01) |

(Continued)

(52) U.S. Cl.
CPC ............... *A61M 39/18* (2013.01); *A61L 2/10* (2013.01); *A61M 1/36222* (2022.05);
(Continued)

(58) Field of Classification Search
CPC .............. A61M 39/18; A61M 1/36222; A61M 2039/167; A61M 39/16; A61M 1/169;
(Continued)

(56) References Cited

U.S. PATENT DOCUMENTS

| | | | |
|---|---|---|---|
| 10,967,113 | B2 | 4/2021 | Suzuki |
| 2013/0303996 | A1 | 11/2013 | Rasooly et al. |

(Continued)

FOREIGN PATENT DOCUMENTS

| | | | |
|---|---|---|---|
| EP | 2175923 | B1 | 3/2017 |
| WO | 2020260089 | A1 | 12/2020 |

OTHER PUBLICATIONS

International Preliminary Report on Patentability issued in corresponding International Patent Application No. PCT/EP2022/077972 mailed Apr. 25, 2024 (with English translation) (8 pages).

(Continued)

*Primary Examiner* — Michael Maskell
(74) *Attorney, Agent, or Firm* — Kilyk & Bowersox, P.L.L.C.

(57) ABSTRACT

The invention relates to an access system P for a medical treatment device, in particular an extracorporeal blood treatment apparatus 1. The invention also relates to a medical treatment device, in particular an extracorporeal blood treatment apparatus 1, comprising such an access system P. The access system according to the invention has a housing body 20 which comprises an outer housing part 21 that is hollow on the inside and that is formed a connection piece 26 for connecting a closure part 36 for the fluid-tight closure of the access system or for connecting a connector 27. The access (Continued)

Figure 1:
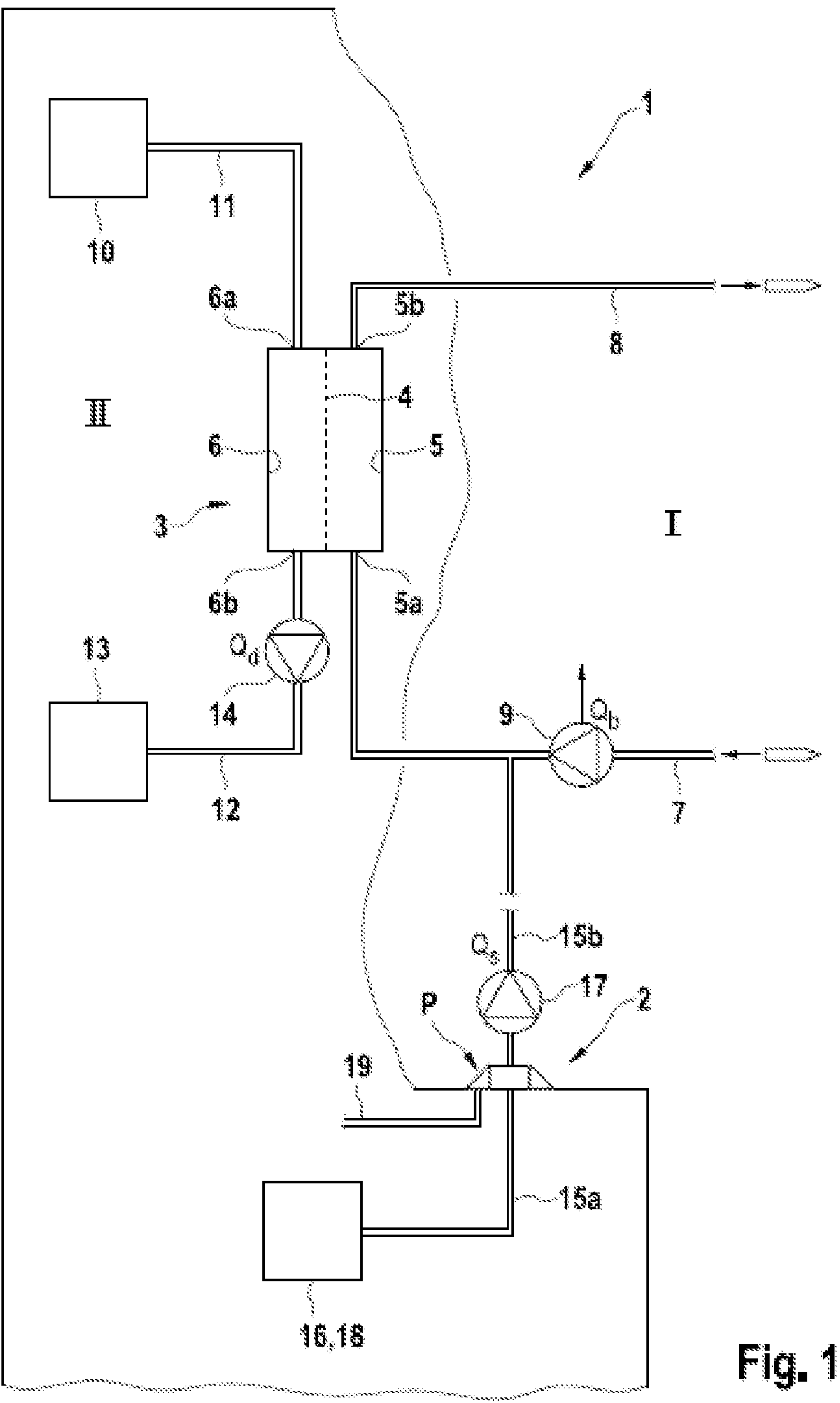

system is characterised in that a UV irradiation unit 30 is provided for emitting ultraviolet light, which comprises a plurality of UV light-emitting diodes 32 emitting ultraviolet light or an annular UV fluorescent tube, the outer housing part 21 having a region which is permeable to ultraviolet light. The UV light-emitting diodes 32 or the annular UV fluorescent tube are arranged in such a way that the ultraviolet light passes through the region of the outer housing part 21 that is permeable to ultraviolet light and enters the interior of the access system.

20 Claims, 6 Drawing Sheets

(51) Int. Cl.
*A61L 103/09* (2026.01)
*A61M 1/36* (2006.01)
*A61M 39/16* (2006.01)

(52) U.S. Cl.
CPC ........ *A61L 2103/09* (2026.01); *A61L 2202/11* (2013.01); *A61M 2039/167* (2013.01)

(58) Field of Classification Search
CPC ... A61M 2205/053; A61M 1/168; A61L 2/10; A61L 2103/09; A61L 2202/11; A61L 2/18; A61L 2103/15
USPC .......................................................... 250/435
See application file for complete search history.

(56) References Cited

U.S. PATENT DOCUMENTS

2014/0138301 A1* 5/2014 Iwahori .............. A61M 1/3646 210/321.72
2014/0334974 A1 11/2014 Rasooly et al.

OTHER PUBLICATIONS

International Search Report and Written Opinion (with English translation of International Search Report) issued in corresponding International Patent Application No. PCT/EP2022/077972 mailed Jan. 31, 2023 (12 pages).

* cited by examiner 27
26
28
28A
23A
31
32B
30
32A
29
32
24
24
P
23
21
20
22
25

27
26
31
32B
30
32A
28
28A
29
23A
32B
32
32A
31
P
24
24
33
23
21
20
22
25

36
37B
26
26B
21A
31
38
32
26A
37A
37
24
24
P
23
21
20
22
25

36
26
37
32
31
38A
38
31
32
P
24
24
23
21
20
22
25

ACCESS SYSTEM FOR A MEDICAL TREATMENT DEVICE FOR EXTRACTING OR ADDING A MEDICAL LIQUID, AND MEDICAL TREATMENT DEVICE HAVING AN ACCESS OF THIS KIND

This application is a National Stage Application of PCT/EP2022/077972, filed Oct. 7, 2022, which claims priority to German Patent Application No. 10 2021 126 702.1, filed Oct. 14, 2021.

The invention relates to an access system for a medical treatment device, in particular an extracorporeal blood treatment apparatus. The invention also relates to a medical treatment device, in particular an extracorporeal blood treatment apparatus, comprising such an access system.

For withdrawing or supplying a fluid, access systems, known as ports, are also used in medical technology that allow sterile connection of the connector of a hose line in order to be able to supply or withdraw a fluid. Access systems of this type are generally located on a front side of the housing of medical devices in order to be easily accessible.

In haemodialysis machines that are set up for haemodiafiltration, the patient's blood is thinned by adding substituate. The substituate can be provided in containers or obtained online in the dialysis machine from dialysate via a sterile filter. Haemodialysis machines are known which have an access system to which the connector of a hose line is connected in order to be able to feed the substituate provided by the dialysis machine to the extracorporeal circuit. When not in use, the access system is tightly closed by a closure cap in order to avoid contamination. Before connecting the connector, the closure cap is removed. For the access system, care must be taken that germs or pathogens that can adhere to the access system in daily practice do not get into the patient's blood. Therefore, the access system is generally flushed with a disinfectant solution. After disinfection, no residues of the disinfectant solution should remain in order to reliably prevent the blood from coming into contact with the disinfectant solution.

U.S. Pat. No. 10,967,113 B2 describes an access system for an extracorporeal blood treatment apparatus having a housing body which comprises an outer cylindrical housing part in which a connection piece for a syringe for withdrawing a fluid is formed. The access system has a closure device with a pivotable closure part which closes the housing opening when the closure part is in front of the opening. The closure device has a UV irradiation unit which is designed to emit ultraviolet light in order to be able to kill germs or pathogens in the region of the housing opening. The closure part is designed as a closure cap which encloses the outer cylindrical housing part in a sealing manner. A UV light-emitting diode which emits ultraviolet light is located in the closure cap, the base of the closure cap being made of a material that is permeable to ultraviolet light, so that the UV rays enter the outer cylindrical housing part in the axial direction through the transparent base. The disadvantage is that not all regions of the access system are irradiated with UV light. In particular, no UV radiation can strike the particularly critical regions in which the closure cap seals with respect to the cylindrical housing part and which are behind the seal and cannot be reached by other disinfections.

EP 2 175 923 B1 discloses a UV irradiation unit having a hinged cylindrical housing in which a plurality of UV light-emitting diodes are integrated which are distributed around the circumference of the cylindrical housing. The irradiation unit is intended to enclose the hose coupling of a fluid line.

The object of the invention is to provide an access system for a medical treatment device, in particular an extracorporeal blood treatment apparatus, which allows germs or pathogens to be killed reliably. In addition, an object of the invention is to create a medical treatment device comprising an improved access system which allows germs or pathogens to be killed reliably. Another object of the invention is to reduce the time required to disinfect the access system.

These objects are achieved according to the invention by the features of the independent claims. The dependent claims relate to preferred embodiments of the invention.

The access system according to the invention for a medical treatment device, in particular an extracorporeal blood treatment apparatus, has a housing body which comprises an outer housing part that is hollow on the inside and that has a connection piece for connecting a closure part for the fluid-tight closure of the access system or for connecting a connector. An outer housing part is understood to mean any part of the housing body which encloses an elongate cavity which can be filled with a fluid or through which fluid can flow. Consequently, the outer housing part need not have the shape of a cylinder or exactly the shape of a cylinder, but can, for example, have an oval shape. The outer housing part can also consist of several parts.

The access system according to the invention is intended in particular for the withdrawal of a medical fluid. However, the access system can also be used to supply a medical fluid. As a result, the opening of the housing body can be used for withdrawing or supplying a medical fluid. The medical fluid can be, for example, substituate. The housing body allows the access system to be attached to a medical device, in particular an extracorporeal blood handling device.

The access system according to the invention is characterised in that the irradiation unit for emitting ultraviolet light comprises a plurality of UV light-emitting diodes emitting ultraviolet light or an annular UV fluorescent tube emitting ultraviolet light, the outer housing part having a region which is permeable to ultraviolet light. The UV light-emitting diodes or the annular UV fluorescent tube emitting ultraviolet light are arranged in such a way that the ultraviolet light passes through the region of the outer housing part that is permeable to ultraviolet light and enters the interior of the access system. Consequently, the irradiation unit for emitting ultraviolet light is not part of the closure part. The irradiation unit is located on the inside of the machine if the access system is provided in the front of the medical device. Since the light-emitting diodes are not provided on the closure part but on the outer housing part, a relatively large number of UV light-emitting diodes can be arranged in different regions of the access system, so that all critical regions can be irradiated with ultraviolet light with sufficient intensity.

The UV light-emitting diodes or the annular UV fluorescent tube are designed in such a way that they can emit light in a wavelength range that allows germs or pathogens to be killed. Such UV light-emitting diodes or fluorescent tubes, which generate a sufficient radiation intensity in the relevant wavelength range, belong to the prior art.

One embodiment of the access system according to the invention provides both disinfection with a disinfectant and the killing of germs and pathogens with ultraviolet light. The housing body of the access system comprises an inner, preferably substantially cylindrical, housing part which is enclosed by the outer housing part to form a cavity, the connector establishing a fluid connection to the inner housing part when the connector is connected to the connection piece of the access system. When the connector is connected, the medical fluid, for example substituate, can flow through the inner housing part into the connector. When the connector is not connected, the cavity is closed in a fluid-tight manner by the closure part. During disinfection, disinfectant fluid flows through the cavity closed by the closure part, so that disinfectant fluid washes around the critical regions of the access. In addition to disinfection with disinfectant fluid, germs and pathogens can also be killed in the critical regions by UV light.

In another embodiment, the UV light-emitting diodes or the annular UV fluorescent tube are arranged on the portion of the outer housing part which faces the inner housing part, so that the ultraviolet light which passes through the region of the outer housing part that is permeable to ultraviolet light and enters the cavity strikes the inner housing part. As a result, the inner housing part in the interior of the cavity is directly irradiated with ultraviolet light.

In a further embodiment, the connector has a line portion which extends into the cavity when the connector is inserted into the connection piece, so that the line portion can be connected to the inner housing part in a fluid-tight manner. In this embodiment, the UV light-emitting diodes or the annular UV fluorescent tube are arranged on the portion of the outer housing part which is in the region of the connection point of the line portion of the connector and the inner housing part when the connector is inserted into the connection piece, so that the ultraviolet light which passes through the region of the outer housing part that is permeable to ultraviolet light and enters the cavity strikes the connection point of the line portion of the connector and the inner housing part. As a result, the inner housing part is directly irradiated with ultraviolet light in the particularly critical region of the connection point.

The line portion of the connector preferably consists of a material that is permeable to ultraviolet light, at least in the region of the connection point, so that the UV light can pass through the line portion. Consequently, this line portion can be irradiated not only on the outside but also on the inside, for example on the sealing surface.

The inner diameter of the inner housing part and the outer diameter of the line portion of the connector can be dimensioned such that the line portion of the connector can be inserted into the inner housing part in order to establish a fluid connection. As a result, the line portion of the connector is enclosed by the inner housing part at the connection point. In this embodiment, the inner housing part consists of a material that is permeable to ultraviolet light, at least in the region of the connection point, so that the UV light can pass through the inner housing part and strike the line portion of the connector. The line portion of the connector preferably also consists of a material that is permeable to ultraviolet light, so that the UV light irradiates not only the outside but also the inside of the line portion of the connector.

The inner diameter of the inner housing part and the outer diameter of the line portion of the connector can, however, also be dimensioned such that the line portion of the connector can be pushed onto the inner housing part in order to establish a fluid connection.

In another embodiment, the connector has a contact protection means which encloses its line portion and extends beyond the line portion. In this embodiment, at least part of the contact protection means consists of a material that is permeable to ultraviolet light, so that the UV light can pass through the contact protection means and strike the inner housing part and/or the line portion of the connector.

In one embodiment, the connection piece is designed in such a way that the closure part or the connector can be inserted into the connection piece sealingly with respect to the inner wall of the connection piece. In this embodiment, the closure part is not designed in the manner of a "closure cap", but in the manner of a closure plug. The UV light-emitting diodes or the annular UV fluorescent tube are arranged on the connection piece of the outer housing part, the region of the outer housing part that is permeable to ultraviolet light being formed by at least a portion of the connection piece. In this alternative embodiment, which can also be combined with the embodiments described above, germs can be reliably killed in the particularly critical region on the inside of the connection piece, which is difficult to access and where residues of fluids can easily accumulate. However, these residues cannot be removed or can only be removed with difficulty with disinfection on the machine side with the disinfectant or manual disinfection on the outside of the machine.

In the case of the access according to the invention, a sufficient number of the UV light-emitting diodes can be distributed around the periphery of the outer housing part. At least two UV light-emitting diodes in each case can be distributed peripherally and one next to the other. The annular UV fluorescent tube can be arranged around the periphery of the outer housing part.

The UV light-emitting diodes or the annular UV fluorescent tube can be inserted into depressions or recesses which are provided on the housing body. Arrays having a relatively large number of UV light-emitting diodes can also be provided.

In a preferred embodiment, the UV irradiation unit is designed as an annular insert part comprising the UV light emitting diodes or an annular UV fluorescent tube and having a region that is permeable to ultraviolet light, which insert part is inserted into the outer housing part and sealed with respect to the outer housing part. Since the UV irradiation unit can thus be produced and handled as a separate component, there are advantages in terms of manufacturing technology.

In a further embodiment, the closure part is formed on the inner side facing the cavity as a reflective body which is designed in such a way that ultraviolet light striking the reflective body radially is reflected in the axial direction. In this embodiment, with UV light-emitting diodes provided on the outer housing body in the region of the connection piece, not only the region of the closure opening but also the region of the connection point between the line portion of the connector and the inner housing body can be irradiated with UV light.

The reflective body is preferably a rotationally symmetrical body which is provided with a coating that reflects ultraviolet light. The reflective body can, for example, have the shape of a cone or truncated cone or a rotationally symmetrical shape with a concave or convex reflective surface. The reflective body can be designed in such a way that the light beams are locally focused on a specific region. For example, the reflective body can be designed as a parabolic mirror. The UV light-emitting diodes can be distributed around the periphery of the reflective surface or the UV fluorescent tube can enclose the periphery of the reflective surface.

The medical treatment device may be a blood treatment apparatus having an extracorporeal blood circuit, which apparatus has a means for providing substituate, the access system being in fluid communication with the means for providing substituate.

Embodiments of the invention will be explained in greater detail below with reference to the drawings.

Figure 2:
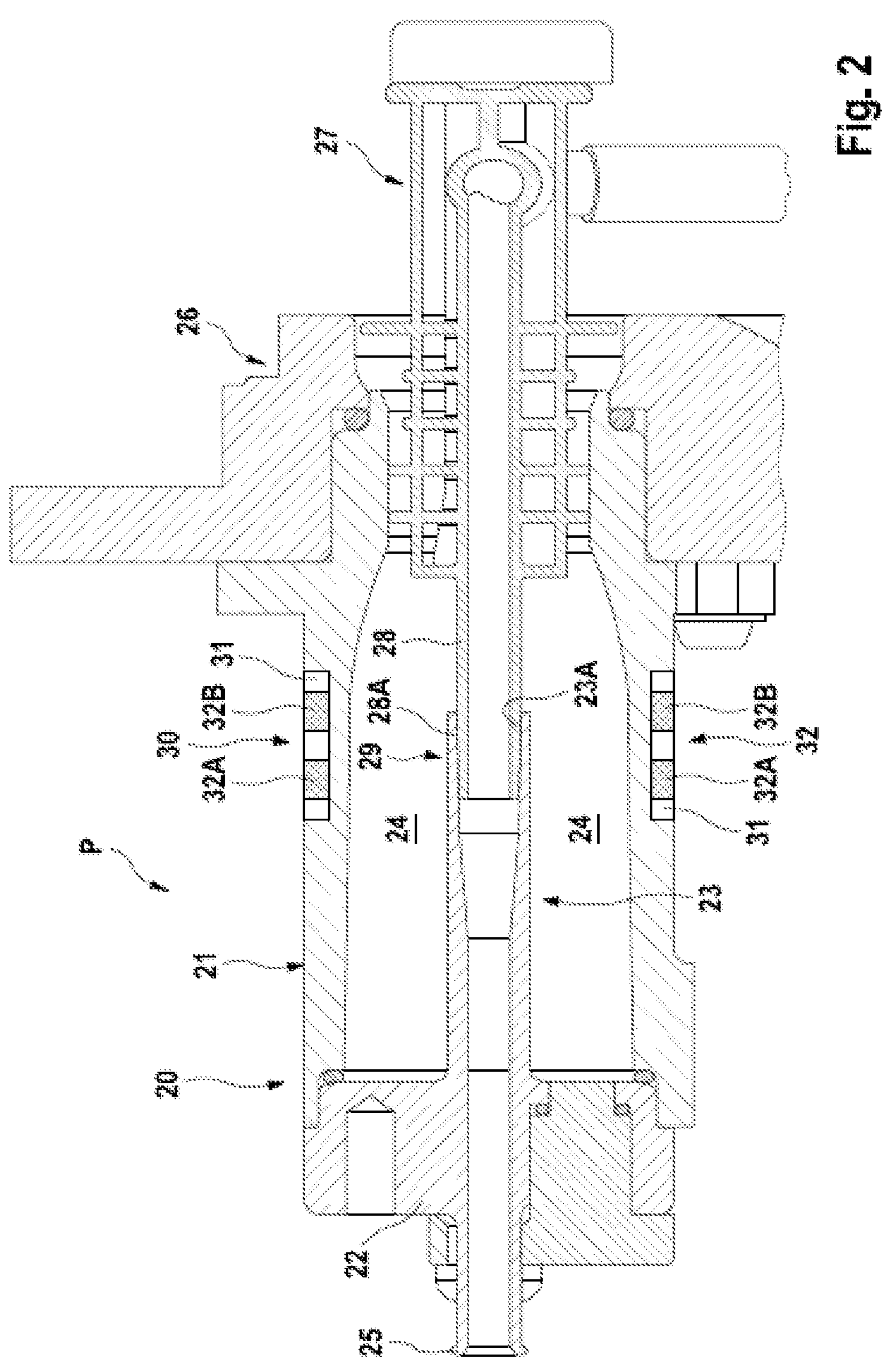
Figure 3:
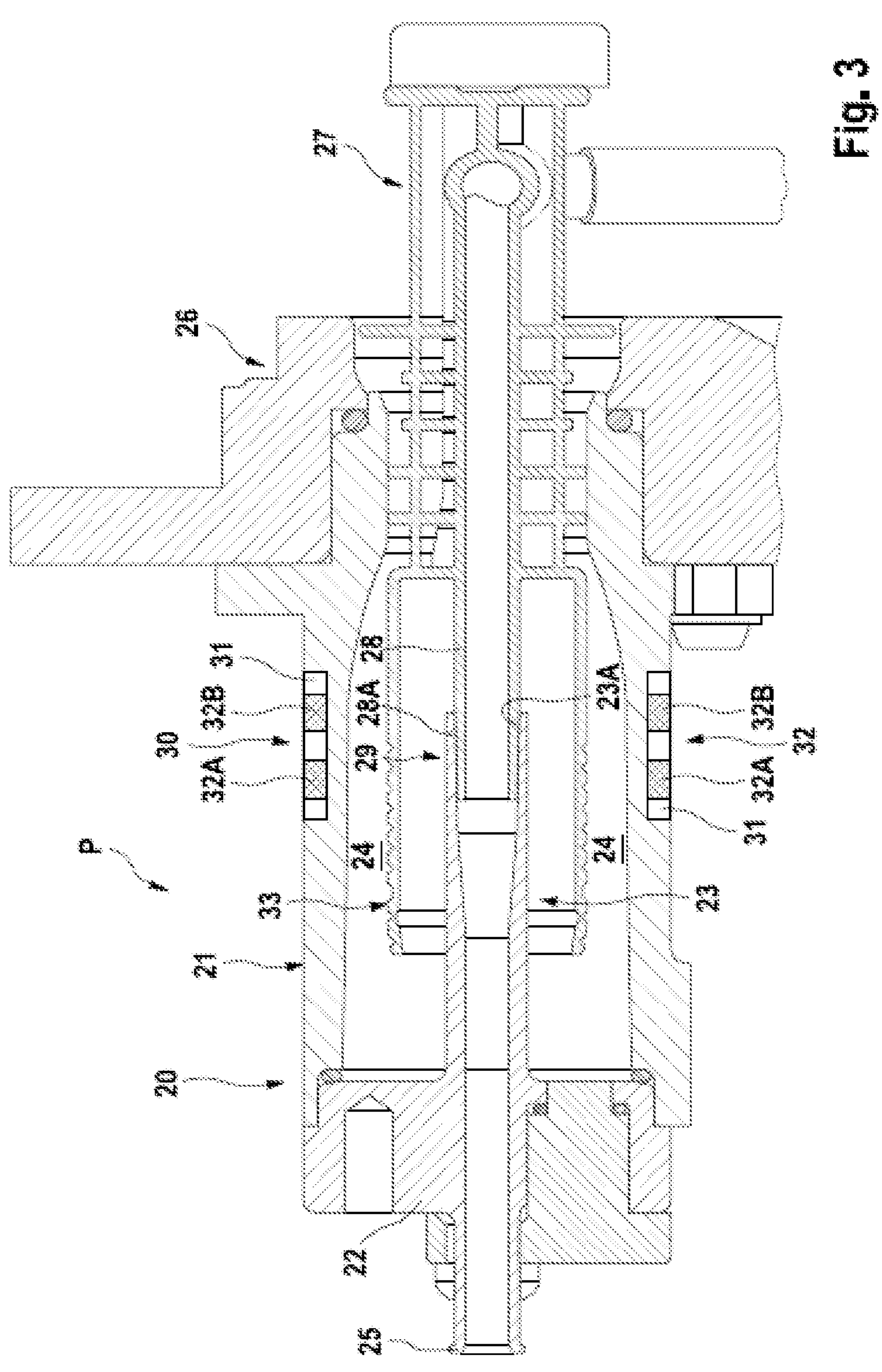
Figure 4:
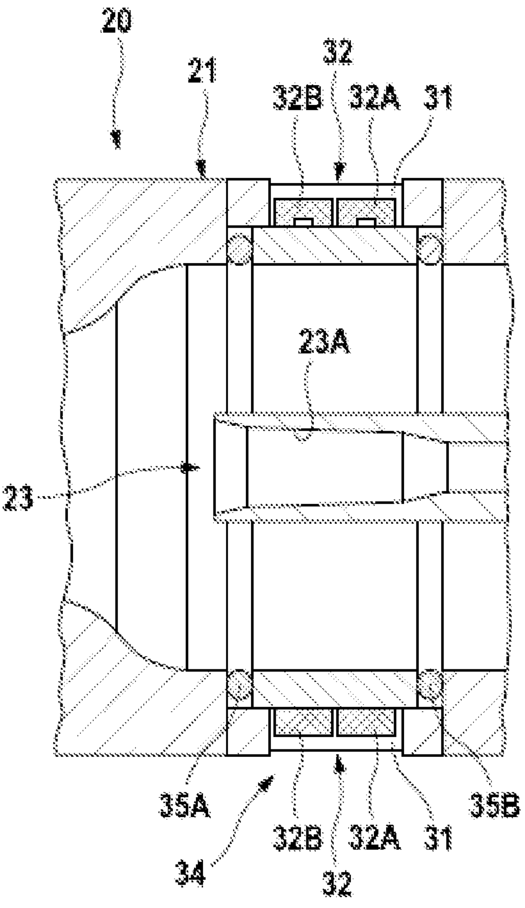
Figure 5:
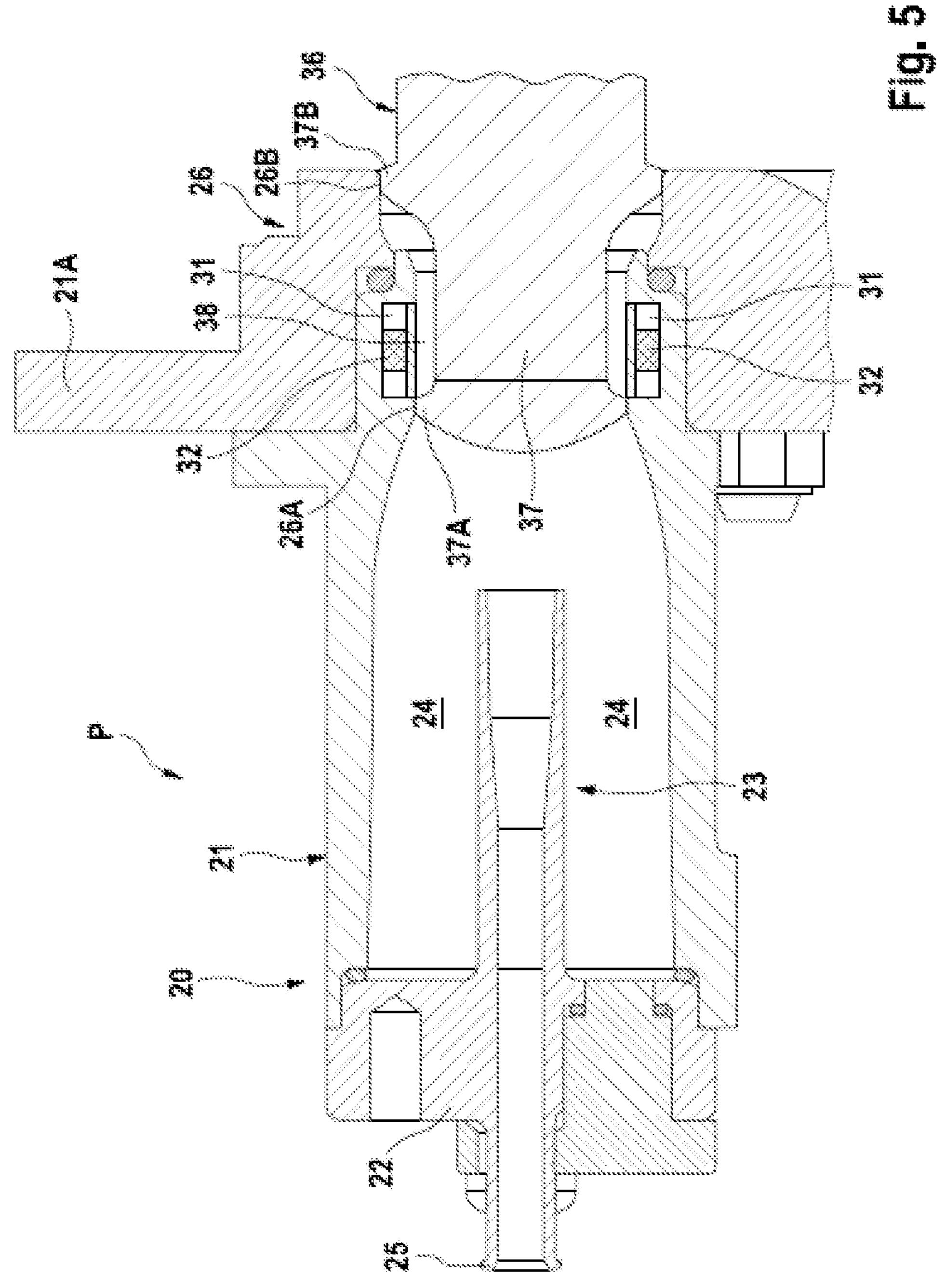
Figure 6:
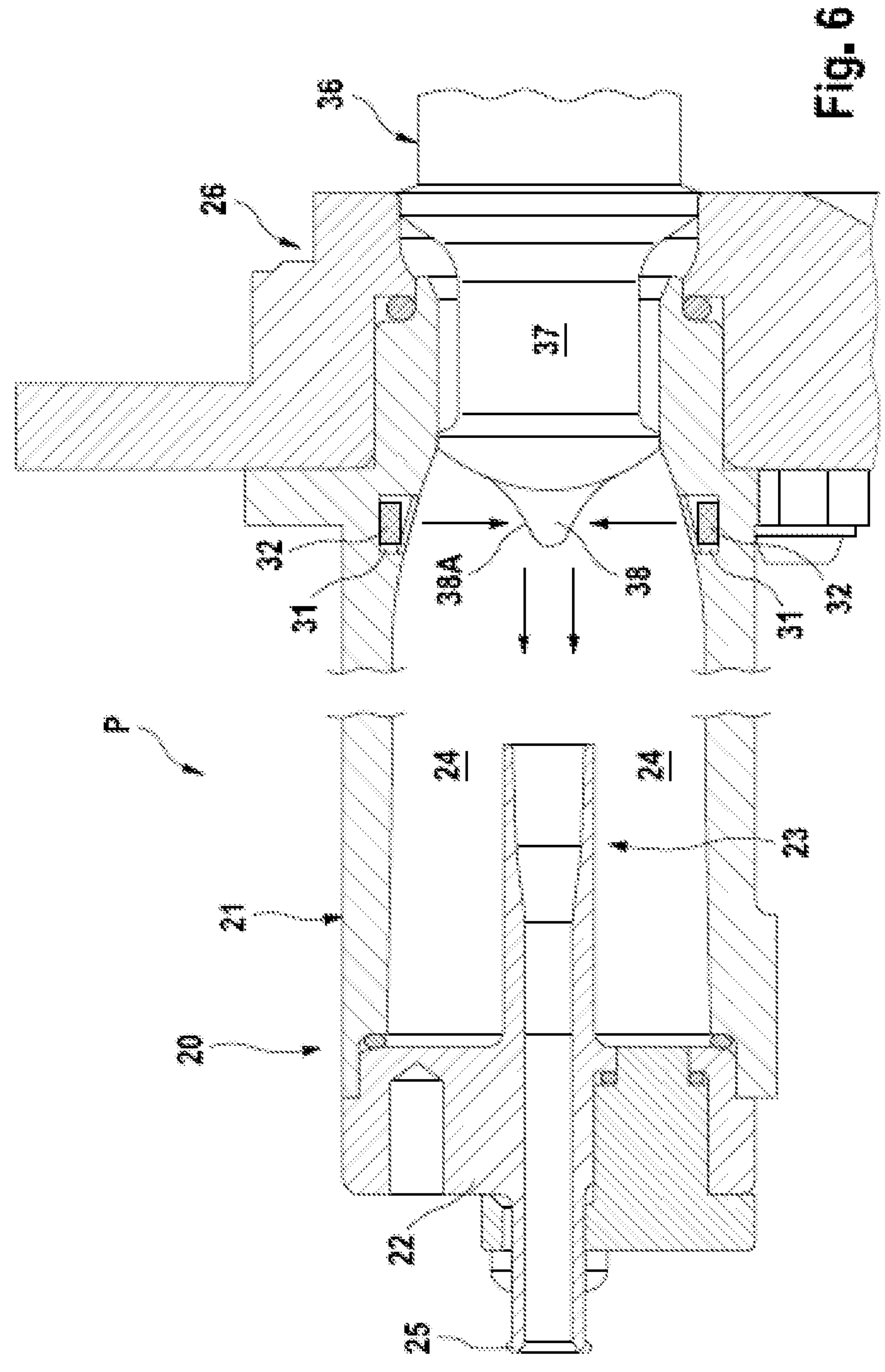

In the drawings:

FIG. 1 is a greatly simplified schematic view of an extracorporeal blood treatment apparatus according to the invention, the blood treatment apparatus comprising the access system according to the invention, FIG. 2 is a sectional view of a first embodiment of the access system according to the invention, FIG. 3 is a sectional view of a second embodiment of the access system according to the invention, FIG. 4 is a sectional view of the UV irradiation unit of a third embodiment of the access system according to the invention, FIG. 5 is a sectional view of a fourth embodiment of the access system according to the invention and FIG. 6 is a sectional view of a fifth embodiment of the access system according to the invention.

As an example of a medical treatment device, FIG. 1 is a greatly simplified schematic view of an extracorporeal blood treatment apparatus 1 having the access system P according to the invention.

The extracorporeal blood treatment apparatus is a haemo (dia)filtration apparatus which has a dialyser 3 that is separated by a semipermeable membrane 4 into a blood chamber 5 through which blood flows and a dialysis fluid chamber 6 through which dialysis fluid flows. The blood chamber 5 is part of an extracorporeal blood circuit I, while the dialysis fluid chamber 4 is part of a dialysis fluid system II of the haemo(dia)filtration apparatus.

The extracorporeal blood circuit I comprises an arterial blood line 7, which leads to the inlet 5*a* of the blood chamber 5, and a venous blood line 8, which branches off from outlet 5*b* of the blood chamber 5 of the dialyser 3. The patient's blood is conveyed through the blood chamber 5 of the dialyser 1 by means of an arterial blood pump 9, which is arranged on the arterial blood line 7. The blood lines 7, 8 and the dialyser 3 form a disposable which is intended for single use and is inserted into the dialysis apparatus for the dialysis treatment.

The fresh dialysis fluid is provided in a dialysis fluid source 10. A dialysis fluid supply line 11 leads from the dialysis fluid source 10 to the inlet 6*a* of the dialysis fluid chamber 6 of the dialyser 3. A dialysis fluid discharge line 12 leads from the outlet 6*b* of the dialysis fluid chamber 6 to a drain 13. A dialysis fluid pump 14 is connected into the dialysis fluid discharge line 12.

During the dialysis treatment, substitution fluid (substituate) can be fed to the extracorporeal blood circuit I via a substituate line 15*b*. In the present embodiment, the substituate line 15*b* is connected to a line portion of the arterial blood line 7. The substituate line 15*b* is part of the disposable intended for single use. To connect a connector of the substituate line 15*b* to the blood treatment apparatus 1, an access system P (port), which is only shown schematically in FIG. 1, is provided on the housing 2 of the blood treatment apparatus, which housing is only indicated in FIG. 1. A fluid line 15*a* connects the access system P to a substituate source 16. The substituate can be a fluid provided in the substituate source 16 and can be conveyed by means of a substituate pump 17. The substituate can be produced online in the extracorporeal blood treatment apparatus. The access system P can also have a further connection for emptying or ventilation.

The access system P can be disinfected before or after a dialysis treatment. In the present embodiment, the disinfectant fluid for disinfecting the access system P is provided in a disinfectant container 18, which can be used in place of the substituate source 16. During the disinfection, the access system P is flushed through with disinfectant fluid, the disinfectant fluid being conducted from the container 18 via the fluid line 15*a* to the access system P and from there being removed again via a return line 19.

A first embodiment of the access system P (port) is described in detail below with reference to FIG. 2.

The access system P has a housing body 20 which is attached to the blood treatment apparatus 1 so as to be freely accessible to the operating personnel. The multi-part housing body 20 comprises an outer cylindrical housing part 21 which is closed in a fluid-tight manner at one end by an end piece 22 and which is open at the other end. The outer cylindrical housing part 21 tapers in the axial direction towards the open end. In addition, the housing body 20 comprises an inner cylindrical housing part 23 which is completely enclosed by the outer cylindrical housing part to form a cavity 24. The inner cylindrical housing part 23 extends from the end piece 22 of the housing body 20 in the axial direction into the cavity 24. A connection 25 for the substituate line 15*b* is provided on the outside of the end piece 21 (FIG. 1). The inner cylindrical housing part 23 is used to transport the substitution fluid or disinfectant fluid.

The open end piece of the housing body 20 is designed as a connection piece 26 into which a suitable connector 27 of the substituate line 15*b* can be inserted to withdraw substituate. The connection piece 26 and the connector 27 are designed in such a way that the outside of the connector is sealed with respect to the inside of the connection piece in a fluid-tight manner when the connector is inserted into the connection piece.

The connector 27 has a line portion 28 which extends into the cavity 24 and which is connected to the inner housing part 23 in a fluid-tight manner when the connector 27 is inserted into the connection piece 26. The inner diameter of the inner cylindrical housing part 23 and the outer diameter of the line portion 28 of the connector 27 are dimensioned such that the line portion of the connector can be pushed into the inner cylindrical housing part 23 in order to establish a fluid connection. The inner cylindrical housing part 23 and the line portion 28 can have conical sealing surfaces 23A, 28A on the outside and inside, respectively. The connection point 29 between the inner cylindrical housing part 23 and the line portion 28 is approximately in the centre of the cavity 24. The connection point 29 can, however, also be arranged offset from the centre of the cavity in the longitudinal direction and/or transverse direction of the outer cylindrical housing part 21.

During dialysis, substituate flows through the inner cylindrical housing part 23 and the line portion 28 of the connector 27 to which the substituate line 15*b* is connected.

For the disinfection of the access system P, the connection piece 26 thereof is closed by a matching closure part, not shown in FIG. 2, which is inserted into the connection piece instead of the connector 27. The disinfectant fluid flows through the inner cylindrical housing part 23 into the cavity 24, so that the interior of the access system is completely filled with disinfectant fluid.

The access system P according to the invention allows not only disinfection with a disinfectant fluid, but also killing germs and pathogens by means of ultraviolet radiation (UV light). For this purpose, a UV irradiation unit 30 is provided, which is part of the housing body 20 in the access system according to the invention.

FIG. 2 shows a first embodiment of the access system P. In this embodiment, the UV irradiation unit 30 is located in the axial direction at the level of the free end of the inner cylindrical housing part 23 in the region of the connection point 29 between the inner cylindrical housing part 23 and the line connection of the connector 27. In this portion, the outer cylindrical housing part 21 has recesses 31 or depressions which are distributed around the periphery and in which UV light-emitting diodes 32 are arranged. In the present embodiment, two UV light-emitting diodes 32A, 32B in each case are located in a recess 31 or depression, which light-emitting diodes are arranged one next to the other in the axial direction. Instead of individual recesses or depressions, however, a peripheral recess or depression can also be provided on the outer outer cylindrical housing body 21, in which the UV light-emitting diodes 32 are distributed around the periphery. Instead of peripherally distributed UV light-emitting diodes 32, an annular UV fluorescent tube emitting UV light can also be provided in a peripheral recess or depression 31 of the outer housing part 21.

The outer cylindrical housing part 21 consists, at least in the region of the recess 31 or depression, of a material permeable to UV light, for example quartz glass, so that the UV light can pass through the outer cylindrical housing part 21 and strike the particularly critical region of the connection point 29. The inside of the outer cylindrical housing part 21 is provided with a coating that reflects ultraviolet light.

Germs can be killed with the access system P according to the invention not only when the connection piece 26 is closed by the closure part 36, but also when the connector 27 is connected to the connection piece 26. In order to disinfect the connection point 29, at least the end piece of the inner housing part 23 must be made of a material that is permeable to UV light, and the end piece of the line portion 28 of the connector 27 can also be made of a material that is permeable to UV light.

FIG. 3 shows a second embodiment of the access system P according to the invention which differs from the embodiment of FIG. 2 by the connector 27. Corresponding parts are provided with the same reference signs. The connector 27 of FIG. 3 has a contact protection means 33 which encloses the line portion 28 and extends in the axial direction beyond the line portion 28.

The contact protection means 33 consists, at least in the region of the connection point 29 of the line portion 28 of the connector 27 and the inner cylindrical housing part 23, of a material that is permeable to ultraviolet light, so that germs can be killed by UV light even if the connector 27 is connected. The UV light can then pass through the contact protection means 28 and strike the connection point 29. If, however, irradiation with UV light is to take place only when the connection piece 26 is closed by a closure part 36, the contact protection means 33 does not need to be transparent to UV light.

FIG. 4 is a partial view of the housing body 20 of an alternative embodiment, the corresponding parts being provided with the same reference signs. An annular insert part 34 made of a material that is permeable to ultraviolet light, for example quartz glass, is inserted into the outer cylindrical housing part 21, on which insert part the UV light-emitting diodes 32A, 32B are distributed around the periphery. The annular insert part 34 is sealed with respect to the cylindrical housing part 23 by sealing rings 35A, 35B.

FIG. 5 shows another embodiment, the corresponding parts being provided with the same reference signs. The connection piece 26 of the outer cylindrical housing part 21 is closed by a closure part 36, of which only the front part is shown in FIG. 5. The closure part 36 has a sealing body 37 which can be inserted in a suitable manner into the opening of the connection piece 26, the outside of the sealing body 37 sealing with respect to the inside of the connection piece 26. In the present embodiment, the sealing body 37 has front and rear annular sealing surfaces 37A, 37B, which bear against the sealing surfaces 26A, 26B of the connection piece 26, forming an annular space 38 therebetween. The sealing body 37 can, however, also have only one front or rear annular sealing surface. In this embodiment, the UV light-emitting diodes 32 or the annular UV fluorescent tube are provided in the connection piece 26 of the outer cylindrical housing part 21. The UV light-emitting diodes 32 or the annular UV fluorescent tube are inserted into a peripheral recess 31 or depression in the connection piece 26, or UV light-emitting diodes 32 can be inserted into individual recesses or depressions that are distributed around the periphery.

The connection piece 26 is transparent to UV light at least in the inner region behind which the UV light-emitting diodes 32 or the annular UV fluorescent tube are arranged. The UV light-emitting diodes 32 or the annular UV fluorescent tube can, for example, be inserted into a groove or recess or depression which is closed by a cover made of a material that is permeable to UV light. The UV light-emitting diodes 32 or the annular UV fluorescent tube irradiate the region of the connection piece 26 which is not accessible for disinfection from the outside. In order to widen the irradiation region, a plurality of rows of UV light-emitting diodes 32 distributed peripherally and one behind the other in the axial direction or a plurality of annular UV fluorescent tubes arranged one behind the other can also be provided. The UV light-emitting diodes 32 can also be arranged in such a way that the region of the sealing surfaces of the connection piece 26 and the closure part 36 is irradiated. The inside of the connection piece 26 and/or the outside of the sealing body 37 can be provided with a coating that reflects UV light. The irradiation is possible at any point in time; the irradiation can take place before the treatment in the idle state and during disinfection and when setting up, even if the port is open.

In the present embodiment, it should be noted that the outer cylindrical housing part 26 does not have to consist of one piece, but can also comprise a portion of a housing part 21A of the medical device.

FIG. 6 shows a further embodiment which differs from the embodiment of FIG. 5 in that a reflective body 38 is provided on the front side of the sealing body 37 of the closure part 36, which reflective body can be an integral part of the sealing body. Corresponding parts are provided with the same reference signs. The reflective body 38 is designed in such a way that ultraviolet light striking the reflective body radially is reflected in the axial direction. For this purpose, for example, the surface of the closure part 36 pointing into the interior of the cavity 24 can be shaped accordingly and provided with a coating 38A that reflects UV light. In this embodiment, UV light-emitting diodes 32 or an annular UV fluorescent tube are provided on the outer cylindrical housing part 21 in the vicinity of the connection piece 26 in the axial direction at the level of the reflective body 38, so that the UV rays strike its reflection surface 28A in the radial direction and are reflected in the axial direction. As a result, the entire cavity 24 can be irradiated with UV light. The inner and/or outer housing part 21, 23 can be provided with a reflective coating. The reflective body 38 can also be designed in such a way that the light beams are focused on specific regions of the cavity 24.

The different arrangements of the UV light-emitting diodes 32 described in the embodiments can also be combined with one another, so that irradiation with UV light takes place from different directions, as a result of which all critical regions can be detected.

The annular irradiation with UV light by means of peripherally arranged UV light-emitting diodes or an annular UV fluorescent tube has the advantage that the radiation intensity over the cross section of the connection piece is equally high, i.e. as high in the centre as in the edge regions, although the radiation intensity of a UV light source decreases sharply with increasing distance. The light beams from the UV light-emitting diodes 32 or the annular fluorescent tube extend in the manner of the field lines inside a ring coil. As a result, when the port is open, all germs that penetrate the port are irradiated with equal intensity.

The invention claimed is:

1. An access system for a medical treatment device having a housing body which comprises an outer housing part that is hollow on the inside and that has a connection piece for connecting a closure part for the fluid-tight closure of the access system or for connecting a connector, the access system comprising a UV irradiation unit which is designed to emit ultraviolet light, wherein the irradiation unit for emitting ultraviolet light comprises a plurality of UV light-emitting diodes emitting ultraviolet light or an annular UV fluorescent tube emitting ultraviolet light, the outer housing part having a region which is permeable to ultraviolet light, and the UV light-emitting diodes or the annular fluorescent tube are arranged in such a way that the ultraviolet light passes through the region of the outer housing part that is permeable to ultraviolet light and enters the interior of the access system.

2. The access system according to claim 1, wherein the housing body comprises an inner housing part which is enclosed by the outer housing part to form a cavity, the connector being able to establish a fluid connection to the inner housing part.

3. The access system according to claim 2, wherein the UV light-emitting diodes or the UV fluorescent tube are arranged on the portion of the outer housing part which faces the inner housing part, so that the ultraviolet light which passes through the region of the outer housing part that is permeable to ultraviolet light and enters the cavity strikes the inner housing part.

4. The access system according to claim 3, wherein the connector has a line portion which extends into the cavity when the connector is inserted into the connection piece, so that the line portion is capable of being connected to the inner housing part in a fluid-tight manner, the UV light-emitting diodes being arranged on the portion of the outer housing part which is in the region of the connection point of the line portion of the connector and the inner housing part when the connector is inserted into the connection piece, so that the ultraviolet light which passes through the region of the outer housing part that is permeable to ultraviolet light and enters the cavity strikes the connection point of the line portion of the connector and the inner housing part.

5. The access system according to claim 4, wherein the line portion of the connector consists, at least in the region of the connection point, of a material that is permeable to ultraviolet light.

6. The access system according to claim 4, wherein the inner diameter of the inner housing part and the outer diameter of the line portion of the connector are dimensioned such that the line portion of the connector is insertable into the inner housing part in order to establish a fluid connection.

7. The access system according to claim 4, wherein the connector has a contact protection means which encloses its line portion and extends beyond the line portion, at least one region of the contact protection means consisting of a material that is permeable to ultraviolet light.

8. The access system according to claim 1, wherein the connection piece of the outer housing part is designed in such a way that the closure part or the connector is insertable into the connection piece sealingly with respect to the inner wall of the connection piece, and the UV light-emitting diodes of the UV fluorescent tube are provided on the connection piece, the region of the outer housing part that is permeable to ultraviolet light being formed by at least one region of the connector.

9. The access system according to claim 1, wherein the UV light-emitting diodes are distributed around the periphery of the outer housing part.

10. The access system according to claim 1, wherein a plurality of UV light-emitting diodes are arranged one next to the other around the periphery of the outer housing part.

11. The access system according to claim 1, wherein the UV irradiation unit is designed as an annular insert part comprising the UV light-emitting diodes or the UV fluorescent tube and having a region that is permeable to ultraviolet light, which insert part is inserted into the outer housing part and sealed with respect to the outer cylindrical housing part.

12. The access system according to claim 1, wherein at least a portion of the inside of the outer housing part is provided with a coating that reflects ultraviolet light.

13. The access system according to claim 1, wherein at least a portion of the inside of the closure part is provided with a coating that reflects ultraviolet light.

14. The access system according to claim 1, wherein the closure part is formed on the inner side facing the cavity as a reflective body which is designed in such a way that ultraviolet UV light striking the reflective body radially is reflected in the axial direction.

15. The access system according to claim 14, wherein the reflective body is a rotationally symmetrical body which is provided with a coating that reflects ultraviolet light.

16. The access system according to claim 1, wherein the outer housing part and/or the inner housing part is a substantially cylindrical housing part.

17. A medical treatment device having an access system according to claim 1.

18. The medical treatment device according to claim 17, wherein the medical treatment device is an extracorporeal blood treatment apparatus having an extracorporeal blood circuit, which apparatus has a means for providing substituate, the access system being in fluid communication with the means for providing substituate.

19. The access system of claim 1, wherein the medical treatment device is an extracorporeal blood treatment apparatus.

20. The access system according to claim 5, wherein the inner diameter of the inner housing part and the outer diameter of the line portion of the connector are dimensioned such that the line portion of the connector is insertable into the inner housing part in order to establish a fluid connection.

* * * * *